US008309939B2

(12) United States Patent
Harada et al.

(10) Patent No.: US 8,309,939 B2
(45) Date of Patent: Nov. 13, 2012

(54) PARTICLE BEAM TREATMENT APPARATUS AND PARTICLE BEAM TREATMENT METHOD

(75) Inventors: Hisashi Harada, Tokyo (JP); Osamu Takahashi, Tokyo (JP); Yue Hu Pu, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 294 days.

(21) Appl. No.: 12/867,387

(22) PCT Filed: May 13, 2008

(86) PCT No.: PCT/JP2008/058749
§ 371 (c)(1),
(2), (4) Date: Aug. 12, 2010

(87) PCT Pub. No.: WO2009/139043
PCT Pub. Date: Nov. 19, 2009

(65) Prior Publication Data
US 2011/0012028 A1   Jan. 20, 2011

(51) Int. Cl.
*A61N 5/10* (2006.01)
(52) U.S. Cl. .................. 250/398; 250/492.1; 250/492.3; 250/505.1
(58) Field of Classification Search ............... 250/492.1, 250/492.3, 398, 505.1
See application file for complete search history.

(56) References Cited

U.S. PATENT DOCUMENTS

| 6,614,038 B1 * | 9/2003 | Brand et al. ............... 250/492.3 |
| 6,736,831 B1 * | 5/2004 | Hartmann et al. ................. 607/1 |
| 7,102,144 B2 * | 9/2006 | Matsuda et al. ........... 250/492.1 |
| 7,560,715 B2 * | 7/2009 | Pedroni ...................... 250/492.3 |
| 2001/0022502 A1 * | 9/2001 | Akiyama et al. .............. 315/503 |
| 2006/0226372 A1 | 10/2006 | Yanagisawa et al. |
| 2007/0181815 A1 | 8/2007 | Ebstein |

FOREIGN PATENT DOCUMENTS

| EP | 1 477 206 | 11/2004 |
| EP | 1 584 353 | 10/2005 |
| JP | 7-136290 A | 5/1995 |
| JP | 8-280823 A | 10/1996 |
| JP | 10-314323 A | 12/1998 |
| JP | 11-000408 A | 1/1999 |
| JP | 2003-294848 A | 10/2003 |
| JP | 2004-358237 A | 12/2004 |
| JP | 2006-280457 A | 10/2006 |
| JP | 2006-341010 A | 12/2006 |
| JP | 2007-075245 A | 3/2007 |

OTHER PUBLICATIONS

Matsufuji et al. Specification of Carbon Ion Dose at the National Institute of Radiological Science (NIRS). J. Radiat. Res., 48: Suppl., A84 (2007).*

(Continued)

*Primary Examiner* — Michael Logie
(74) *Attorney, Agent, or Firm* — Buchanan Ingersoll & Rooney PC

(57) ABSTRACT

When a predetermined region of a target volume is divided into multiple layers in a depth direction of particle beams and particle beams are irradiated, dose calibration is carried out separately for the divided layers.

6 Claims, 7 Drawing Sheets

OTHER PUBLICATIONS

Haberer et al., "Magnetic Scanning System for Heavy Ion Therapy" Nuclear Instruments & Methods in Physics Research, Section—A: Accelerators Spectrometers, Detectors and Associated Equipment, Elsevier, Amsterdam, NL, (1993), vol. A330, No. 1/02, pp. 296-305.
Supplementary European Search Report dated Jun. 6, 2011, issued in the corresponding European Patent Application No. 08752629.9-2305.
International Search Report (PCT/ISA/210) issued on Jul. 1, 2008, by Japanese Patent Office as the International Searching Authority for International Application No. PCT/JP2008/058749.
Barbara Schaffner et al., "Ridge Filter Design and Optimization for the Broad-Beam Three-Dimensional Irradiation System for Heavy-Ion Radiotherapy", Med. Phys., vol. 27, No. 4, Apr. 2000, pp. 716-724, Am. Assoc. Phys. Med.

* cited by examiner

PARTICLE BEAM

PARTICLE BEAM TREATMENT APPARATUS AND PARTICLE BEAM TREATMENT METHOD

TECHNICAL FIELD

The present invention relates to a particle beam treatment apparatus and a particle beam treatment method which irradiates particle beams to treat cancer or the like.

BACKGROUND ART

According to a known particle beam irradiation method which is called laminated irradiation or scanning irradiation, a target volume (also simply referred to as a target) is divided in the beam traveling direction of particle beams and particle beams are irradiated.

In order to obtain a desired particle beam distribution in a depth direction, it is necessary to set a dose weight of each layer of the target volume to a desired value.

For this reason, dose calibration is carried out before irradiation. According to the related art, dose calibration is carried out at one point, that is, at the center of the SOBP (Spread Out Bragg Peak: Enlarged Bragg Peak) in the depth-direction distribution of the biological dose.

For example, Patent Citation 1 (JP-A-2004-358237) describes that "a target is divided into multiple layers and the irradiation amount is determined separately for the layers". Patent Citation 2 (JP-A-10-314323) describes that "a target is divided into multiple layers and the irradiation amount is determined uniformly for the layers".

Non-Patent Citation 1 describes that "the weight of a mini-ridge filter used in laminated irradiation is designed to show a Gaussian distribution, thereby easing the effect of interlayer position errors".

The "SOBP" and "mini-ridge filter" will be described below in the description of embodiments of the invention.

Patent Citation 1: JP-A-2004-358237
Patent Citation 2: JP-A-10-314323
Non-Patent Citation 1: Ridge filter design and optimization for the broad-beam three-dimensional irradiation system for heavy-ion radiation therapy. Barbara Schaffner, Tatsuaki Kanai, Yasuyuki Futami, and Munefumi Shimbo, Med. Phys. Volume 27(4), April 2000, pp 716-724.

DISCLOSURE OF INVENTION

Technical Problem

Hitherto, in laminated irradiation, dose calibration is carried out at one representative point, that is, at the center of the SOBP, like extended irradiation of the related art.

In contrast, in laminated irradiation, since the instrument setting differs between the layers, it is natural to consider that there is a dose calibration factor for each layer, and there is a problem in that calibration at one point, that is, at the center of the SOBP is insensitive to the calibration factor of a shallow layer.

When a calibration factor is actually measured for each layer, since change in the depth direction of a Bragg curve is steep, a significant error occurs in a dose calibration value due to a slight position error of a location where a dosimeter is provided, and it is difficult to carry out dose calibration accurately in a short time for each layer.

The term "Bragg curve" means a curve which, when a charged particle beam (for example, proton beam or carbon beam) is irradiated onto an object to be irradiated, represents a relative dose given into the object to be irradiated until the charged particles reach, and has a peak near the deepest portion.

The position error in the depth direction is caused by insufficient mechanical accuracy of a dose distribution measurement apparatus used in dose calibration, an error due to the shape of the dosimeter used in calibration not having a two-dimensional plane, an effective thickness error of a material, such as a dose monitor on the beam line.

For these causes, even when calibration is carried out at the peak of the Bragg curve, calibration may be actually carried out outside the peak, and it may be difficult to obtain accuracy of the calibration factor.

The invention has been finalized in order to solve such problems, and an object of the invention is to provide a particle beam treatment apparatus which can carry out dose calibration for each layer in laminated irradiation and can improve accuracy of dose calibration in laminated irradiation.

Technical Solution

The invention provides a particle beam treatment apparatus in which, when a predetermined region of a target volume is divided into multiple layers in a depth direction of particle beams and particle beams are irradiated, dose calibration is carried out separately for the divided layers.

The invention also provides a particle beam treatment apparatus in which, when a predetermined region of a target volume is divided into multiple layers in a depth direction of particle beams and particle beams are irradiated, dose calibration is carried out separately for the divided layers. A physical dose distribution in the depth direction has a region, in which the dose becomes constant by using a mini-ridge filter, in at least a part of the width of each layer, and the dose calibration is carried out.

The invention also provides a particle beam treatment apparatus in which, when a predetermined region of a target volume is divided into multiple layers in a depth direction of particle beams and particle beams are irradiated, dose calibration is carried out separately for the divided layers. A physical dose distribution in the depth direction has a region, in which the dose becomes constant by using a mini-ridge filter, in at least a part of the width of each layer, and the target volume is irradiated while the layers are superimposed.

The invention also provides a particle beam treatment method in which, when a predetermined region of a target volume is divided into multiple layers in a depth direction of particle beams and particle beams are irradiated, dose calibration is carried out separately for the divided layers.

Advantageous Effects

According to the invention, it is possible to ensure calibration accuracy of a shallow layer, and to confirm a variation of the calibration factor for each layer. Thus, even when there is a problem, systematic understanding can be achieved. Further, it is possible to significantly ease position accuracy necessary for dose calibration, and to carry out dose calibration for each layer in laminated irradiation accurately in a short time.

Therefore, according to the invention, it is possible to carry out dose calibration for each layer in laminated irradiation, and to improve accuracy of dose calibration in laminated irradiation.

EXPLANATION OF REFERENCES

Figure 1:
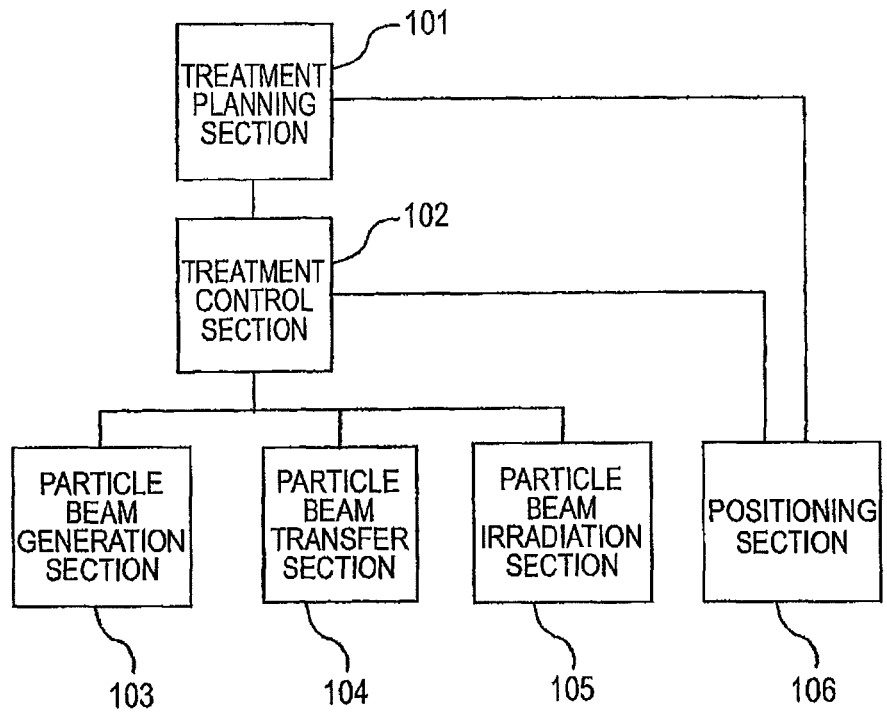
FIG. 1 is a diagram showing the configuration of a particle beam treatment apparatus.

1: lateral-direction irradiation field forming section
2: dose monitor
3: depth-direction irradiation field forming section
4: ridge filter
5: data processing section
21: patient
22: treatment table
61: ridge filter attachment pedestal
62: passage hole (passage port)
70: dosimeter calibration device
71: water phantom
72: dosimeter
73: dosimeter drive device
74: dosimeter circuit and data processing device
101: treatment planning section
102: treatment control section
103: particle beam generation section
104: particle beam transfer section
105: particle beam irradiation section
106: positioning section

BEST MODE FOR CARRYING OUT THE INVENTION

Embodiment 1

An embodiment of the invention will be described with reference to the drawings.

FIG. 1 is a diagram showing the configuration of a particle beam treatment apparatus.

As shown in FIG. 1, the particle beam treatment apparatus includes a treatment planning section 101, a treatment control section 102, a particle beam generation section 103, a particle beam transfer section 104, a particle beam irradiation section 105, a positioning section 106, and the like.

The particle beam irradiation section 105 has a function to form an appropriate irradiation field when particle beams are irradiated onto a patient. The treatment planning section 101 has a function to determine the parameters of respective devices of the particle beam irradiation section 105 as an appropriate value so as to irradiate a desired dose distribution. The positioning section 106 has a function to fix the patient, to position and confirm a target (also referred to as a target volume), and the like.

The treatment control section 102 controls the operations of the particle beam generation section 103, the particle beam transfer section 104, the particle beam irradiation section 105, and the positioning section 106 on the basis of an instruction from the treatment planning section 101.

Figure 2:
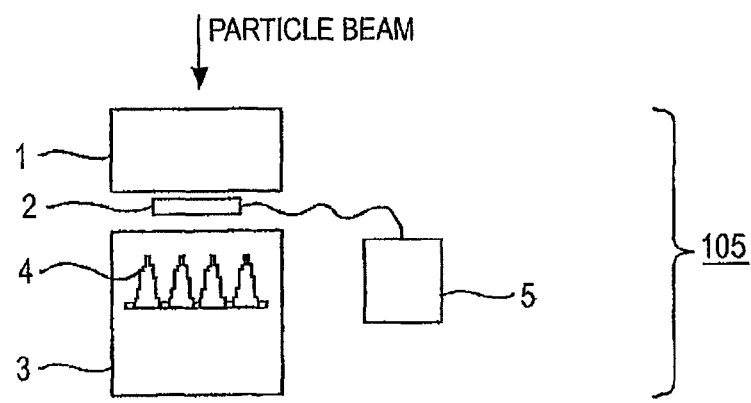
FIG. 2 is a diagram showing an example when particle beams are irradiated from a particle beam irradiation section onto a patient.
Figure 2:
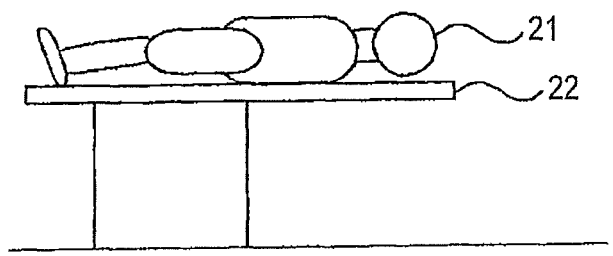

FIG. 2 is a diagram showing an example when particle beams are irradiated from the particle beam irradiation section onto a patient.

As shown in FIG. 2, the particle beam irradiation section 105 includes a lateral-direction irradiation field forming section 1 which controls beams mainly in the lateral direction of an irradiation field of particle beams (that is, at the surface perpendicular to the traveling direction of the beams), a dose monitor 2 which monitors (counts) the dose of the particle beams, a depth-direction irradiation field forming section 3 which controls beams in the depth direction (that is, in the traveling direction of the beams), ridge filters 4 which are formed in the depth-direction irradiation field forming section 3, a data processing section 5 which processes data of the dose counted by the dose monitor 2, and the like. In FIG. 2, reference numeral 21 denotes a patient, and reference numeral 22 denotes a treatment table.

Next, control of beams (that is, particle beams) in the depth direction will be described.

When monoenergetic beams are irradiated, the dose distribution in the depth direction within the body of the patient 21 is called a PDD (Percentage Depth Dose).

If particle beams are irradiated onto a uniform medium, the particle beams are stopped at a depth according to energy when being input to the medium, and the depth at that time is referred to as a range.

The PDD from the surface of the medium to the range has a shape with a peak which is called a Bragg curve, and a portion near the maximum value of the curve (that is, the Bragg curve) is called a Bragg peak.

Figure 3:
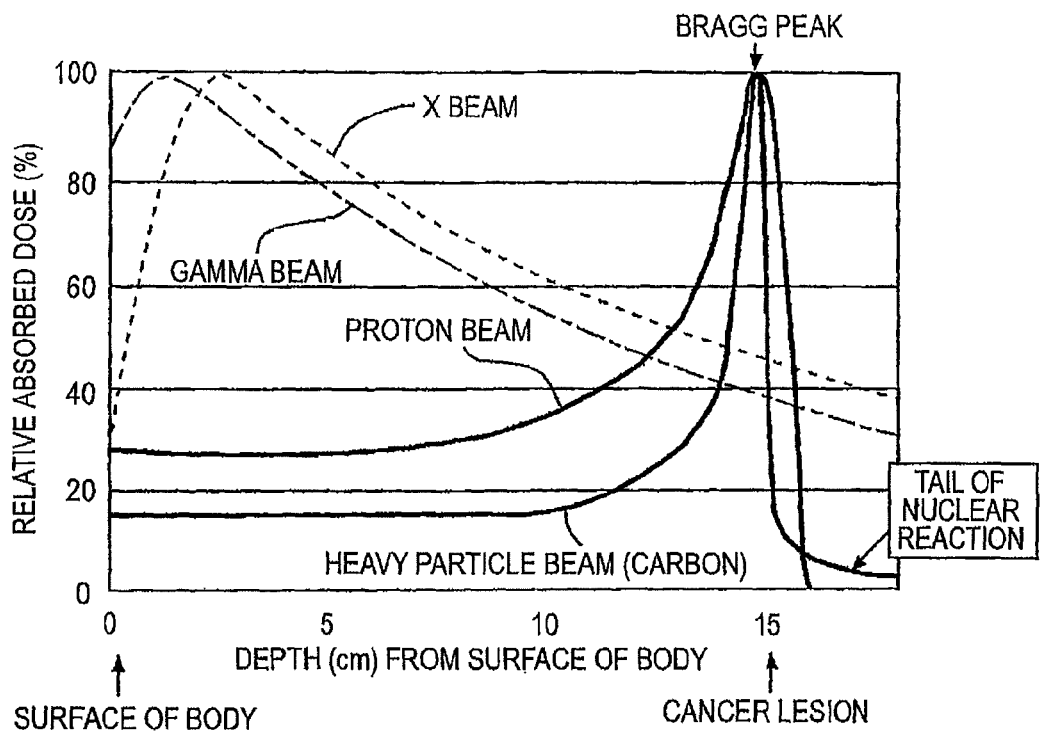
FIG. 3 is a diagram showing a Bragg curve in the case of proton beams and carbon beams.

FIG. 3 is a diagram showing a Bragg curve in the case of proton beams and carbon beams (heavy particle beams).

In FIG. 3, the horizontal axis represents a depth (cm) from the surface of the body, and the vertical axis represents a relative absorbed dose (%).

The shape of the Bragg curve varies depending on the type of nucleus of the particle beams to be irradiated. The proton beams have the width of the Bragg peak greater than the carbon beams.

The carbon nucleus undergoes nuclear fragmentation, but the proton beams do not undergo nuclear fragmentation. For this reason, the dose distribution of the proton beams has no tail (that is, the tail of nuclear reaction).

Hereinafter, although a case where particle beams are carbon beams will be described, the invention may be applied similarly to the proton beams or other types of nucleus.

Figure 4:
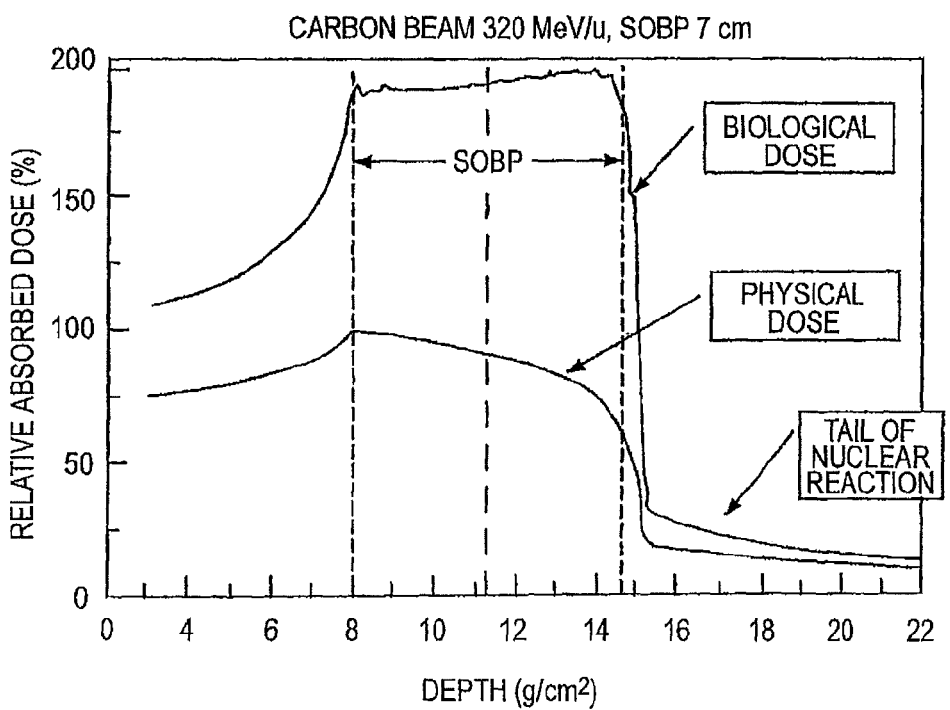
FIG. 4 is a diagram showing an extended Bragg peak of carbon beams.

FIG. 4 is a diagram showing an extended Bragg peak of carbon beams.

According to the extended irradiation method which is a known irradiation technique, the width of the Bragg peak is extended by using a device, called a ridge filter described below. A region, an extended Bragg peak (SOBP) shown in FIG. 4, is formed in which the dose is uniform, and irradiation is carried out.

The width of the SOBP is formed in accordance with the thickness of a target (target volume) in the depth direction.

Next, a difference between a biological dose and a physical dose shown in FIG. 4 will be described.

With regard to the dose, two kinds of a physical dose and a biological dose (also referred to as an effective dose) are defined.

The physical dose refers to energy which is provided to a portion of the target. The unit of the physical dose is gray (Gy).

In contrast, the biological dose is a value which is determined in consideration of the biological effect on the cells based on the physical dose. The unit of the biological dose is gray equivalent (GyE).

The biological dose is defined, for example, on the condition that the dose is equivalent to the irradiation dose by cobalt 60 such that the survival rate of the cells is 10%.

In the case of particle beam treatment, a prescription dose is defined by the biological dose.

The SOBP is to obtain a uniform irradiation effect and defined by the biological dose distribution.

In contrast, in a dosimeter for use in dose calibration, since the measurement of the biological effect is impossible, dose calibration is carried out by using the physical dose.

A known method is used to obtain the biological dose from the physical dose, and description thereof will be omitted.

The SOBP is formed by using a device which is called a ridge filter.

Figure 5:
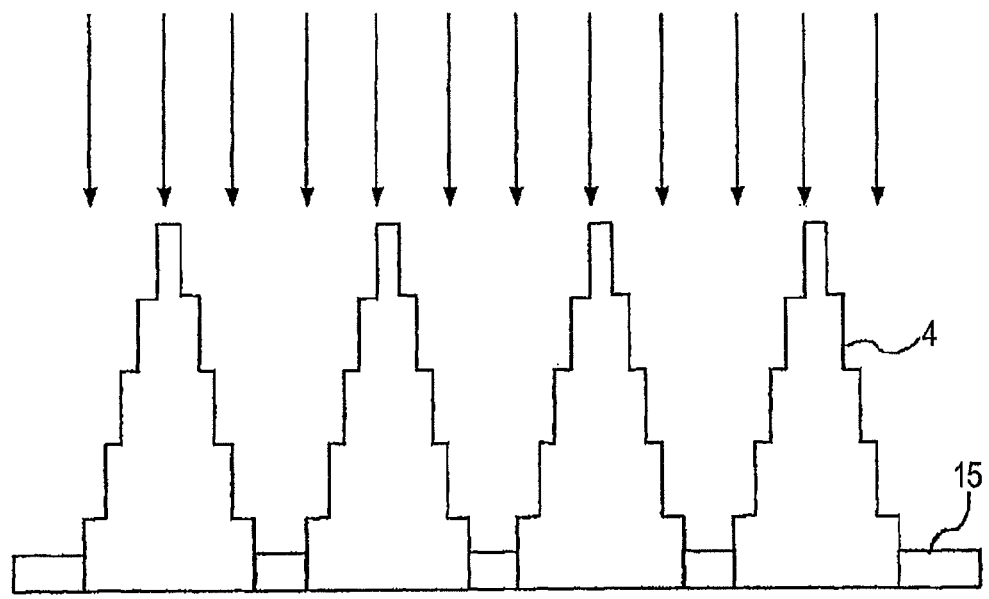
FIG. 5 is a diagram illustrating the principle of a ridge filter.

FIG. 5 is a diagram illustrating the principle of a ridge filter.

As a ridge filter, there are known types of a bar ridge filter shown in FIG. 5 or a modulation wheel. Here, these are collectively called ridge filters.

FIG. 5 is a conceptual view illustrating ridge filters. Actually, the number of ridges is greater. The ridge filters 4 have regions having different thicknesses and widths.

The particle beams pass through different thicknesses in accordance with locations through which the particle beams pass and thus have different ranges.

For example, if a particle beam having a water-equivalent range of 30 cm passes through a portion of the ridge filter having a water-equivalent thickness of 5 cm, the range of the particle beam becomes about 25 cm in water equivalent.

For convenience at the time of manufacturing, actually, the thickness of each of the ridge filters 4 is designed in accordance with a certain step. The ratio of the number of particles of the water-equivalent range is controlled in steps.

Thus, the ratio is called a weight.

For example, if the width of a portion where the thickness of each of the ridge filters 4 is 5 cm in water equivalent is extended, the ratio of a particle beam having the range of about 25 cm in water equivalent can be increased.

In this way, the weight is appropriately selected by the known method, such that a ridge filter can be designed which corresponds to the SOBP having a peak with a uniform biological dose.

Figure 6:
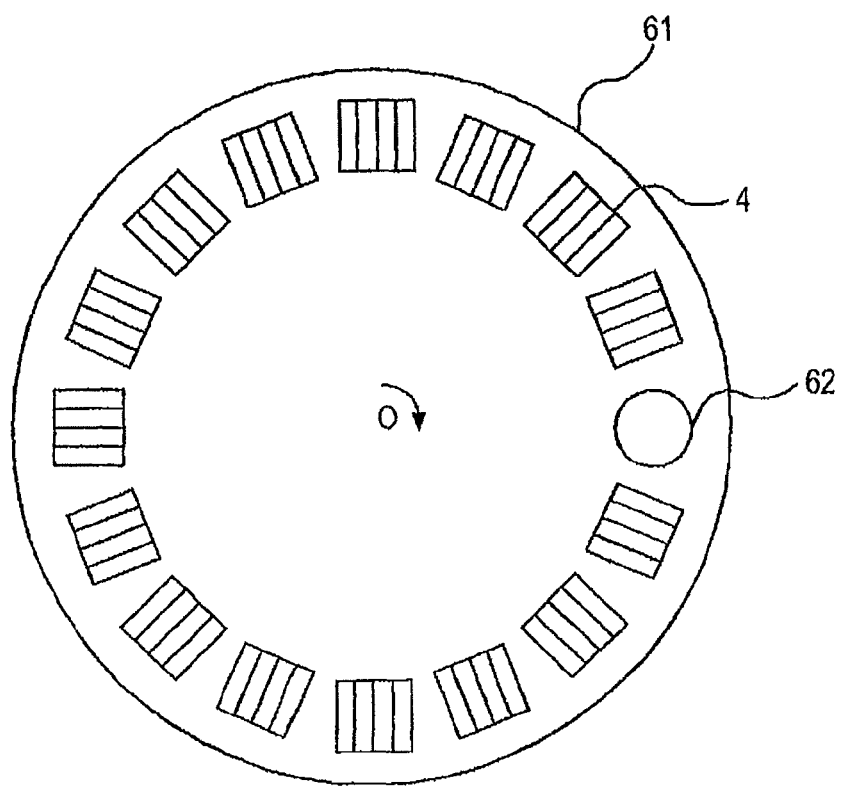
FIG. 6 is a diagram showing the configuration of a ridge filter attachment pedestal.

FIG. 6 is a diagram showing the configuration of a ridge filter attachment pedestal. The ridge filters 4 are mounted on a ridge filter attachment pedestal 61 shown in FIG. 6. Usual ridge filters or several kinds of mini-ridge filters can be mounted simultaneously on the ridge filter attachment pedestal (ridge filter replacement pedestal) 61. The ridge filter attachment pedestal 61 has a structure in which replacement can be easily made.

If a passage hole (passage port) 62 is provided at one location of the ridge filter attachment pedestal 61, non-modulated particle beams can be irradiated.

Hitherto, although an irradiation technique, called a known extended irradiation method, has been described, there is a different known irradiation technique, called laminated irradiation (see Document 1).

According to this method, the target volume is divided into regions in the depth direction, that is, into layers having certain widths, and irradiation is carried out for the regions separately and sequentially. At this time, the widths of the layers do not need to be constant.

With regard to the method of adjusting the depth of each layer, there are two kinds of methods of a method in which the depth of each layer is adjusted by changing energy of an accelerator in the particle beam generation section 103, and a method in which the depth of each layer is adjusted by inserting a necessary number of plates having a given thickness, called range shifters, in the particle beam irradiation section 105.

When particle beams are irradiated, particle beams may be irradiated with the Bragg curve being shifted in steps as it is. If the width of the Bragg peak is narrow, the step width is fine and the number of steps increases, which causes complexity.

For this reason, usually, a method is used which intentionally extends the Bragg peak to extend the step width slightly, and carries out irradiation. The step width is equal to and greater than 2 mm and about 10 mm.

At this time, the extended Bragg peak is referred to as a mini-peak, and a device for forming the mini-peak is called a mini-ridge filter.

It has been proposed that, in the case of laminated irradiation, a mini-ridge filter is used and a mini-peak having a flat weight is used or a mini-peak having a weight in a Gaussian distribution is used.

However, according to the proposal of the related art, the terms "flat" and "Gaussian distribution" discuss the function of the weight itself. However, this proposal does not describe the PDD (Percentage Depth Dose) shape of the physical dose and the object to facilitate dose calibration.

Thus, according to the proposal of the related art, even when the weight of the mini-ridge filter is flat, the physical dose distribution of the mini-peak is not flat, and it is necessary to accurately specify a portion of the mini-peak at which calibration is carried out.

Further, there is a problem in that a significant error occurs in the dose calibration value due to a slight position error in the depth direction.

Next, a method for dose calibration in laminated irradiation will be described.

In the laminated irradiation, the relative dose of each layer, that is, the weight of each layer, needs to be irradiated in accordance with the output of dose calculation which is carried out by the treatment planning section 101 in advance. Otherwise, a desired ETD is not obtained.

In the particle beam treatment apparatus, the dose which is given to each layer is managed as designed on the basis of the count value of the dose monitor 2 provided in the particle beam irradiation section 105.

That is, when irradiation is carried out for a certain layer, the dose given to the relevant layer is converted to the count value of the dose monitor 2. Then, when the count value reaches a desired value, irradiation is temporarily stopped, the counter is reset, and irradiation is carried out for the next layer.

However, the count value of the dose monitor 2 is in arbitrary unit, thus it is not usual to directly manage the physical dose or the biological dose by the count value.

One reason is that, when the device setting of the particle beam irradiation section 105 changes depending on the irradiation condition, the constant relationship between the count value and the physical dose is not constantly ensured.

Figure 7:
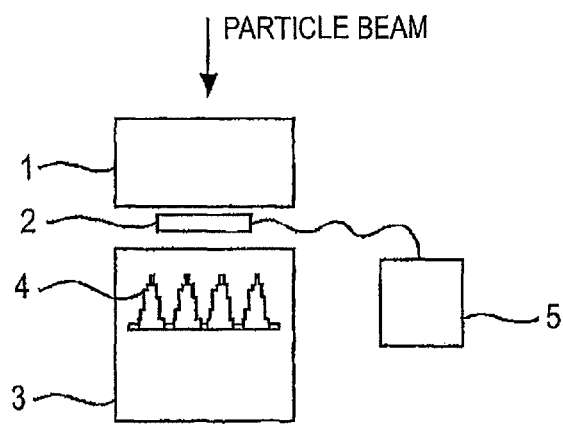
FIG. 7 is a diagram showing the configuration of a particle beam irradiation section and a dosimeter calibration device.
Figure 7:
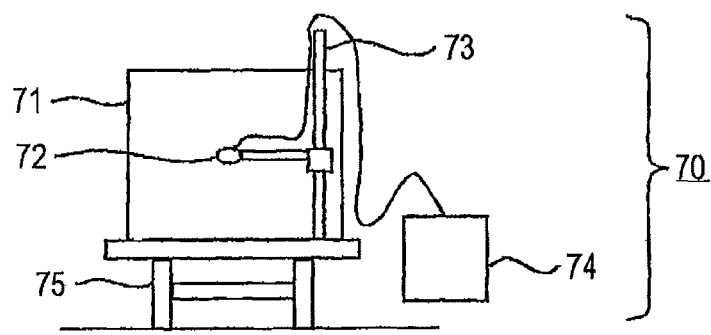

Instead, the count value of the dose monitor 2 is calibrated with respect to the dosimeter 72 by using a device shown in FIG. 7 on a desired irradiation field condition.

FIG. 7 is a diagram showing the particle beam irradiation section 105 and a dosimeter calibration device.

As shown in FIG. 7, a dosimeter calibration device 70 includes a water phantom (that is, a water tank for dose measurement) 71, a dosimeter 72, a dosimeter drive device 73, a dosimeter circuit and data processing device 74, and a pedestal 75.

The dosimeter 72 with calibration guaranteed is used, and a calibration operation is carried out for each patient (for each treatment plan).

In the dose calibration, the physical dose measured by the dosimeter 72 and the count value measured by the dose monitor 2 can be measured. The ratio between the two numerical values is a calibration factor, that is, Gy/count (gray per count).

In the dosimeter 72, while the biological dose is not measured, only the physical dose is measured. Thus, calibration is carried out for the physical dose.

Although the prescription dose is defined by the biological dose, if the PDD of the physical dose corresponding to the prescription dose is calculated, dose calibration and treatment irradiation dose management may be carried out for the PDD of the physical dose. Thus, it is not necessary to become conscious of the biological dose at the time of dose calibration.

Next, description will be provided assuming a specific example.

For example, it is assumed that laminated irradiation is carried out for a spherical target having a diameter of 75 mm.

If it is assumed that the step of each layer is 2.5 mm, 29 layers are required to carry out irradiation to 75 mm in the depth direction.

In the laminated irradiation of the related art, dose calibration is carried out at one point on the center of the entire SOBP which is formed when all of the 29 layers have been irradiated.

This is based on the point of view of the extended irradiation method of the related art.

When being expressed in mathematical form, the physical dose at the center of the SOBP is expressed by the following equation.

$$DSOBP\_PHYS(zC) = K0 \cdot \Sigma d\text{MINIPEAK\_PHYS}(zC+zi) \cdot Wi$$

In the above-described equation, "DSOBP_PHYS(zC)" is a function which represents an SOBP distribution, and denotes a physical dose which is represented by gray.

"dMINIPEAK_PHYS" is a physical dose PDD curve of a mini-peak.

zC denotes the center position of the SOBP, and zi denotes the shift amount of an i-th layer. $\Sigma$ represents the sum of all of the layers, that is, for i=1 and 29.

It is assumed that Wi is the weight of each layer and is standardized as $\Sigma Wi=1$.

K0 denotes a normalization factor, and the value of K0 is determined so as to coincide with a physical dose converted from a prescription dose of single irradiation by DSOBP_PHYS(zC).

In the above-described equation, the PDD curve of the mini-peak is expressed by an expression, which is obtained by superimposing the function of dMINIPEAK_PHYS (zC+zi) such that the shape of the curve is unchanged by shift according to the layer to be irradiated.

Even when this assumption is broken, if an index i is added to the function, the conclusion is unchanged.

For example, when irradiation is prescribed with the prescription dose at the center of the SOBP of 5 GyE, if the physical dose DSOBP_PHYS (zC) at the center of the SOBP is, for example, 2.05 Gy, a calibration factor $\alpha 0$ can be expressed by the following expression.

$$DSOBP\_PHYS(zC) = \alpha 0 \cdot K0 \cdot \Sigma \{d\text{MINIPEAK\_PHYS}(zC+zi) \cdot Wi/\alpha 0\} = 2.05 \text{ Gy}$$

At this time, "$K0 \cdot \Sigma \{d\text{MINIPEAK\_PHYS}(zC+zi) \cdot Wi/\alpha 0\}$" corresponds to the count value measured by the dose monitor. $\alpha 0$ is a calibration factor which is determined by dose calibration, and the unit of $\alpha 0$ is Gy/count.

Hitherto, although the calibration method of the related art has been described, according to the invention, calibration is carried out separately for the layers.

At this time, a physical dose at an arbitrary depth z can be expressed by the following expression.

$$DSOBP\_PHYS(z) = K0 \cdot \Sigma \{\alpha i \cdot d\text{MINIPEAK\_PHYS}(z+zi) \cdot Wi/\alpha i\}$$

Here, $Di(z) = K0 \cdot \alpha i \cdot \text{MINIPEAK\_PHYS}(z+zi) \cdot Wi/\alpha i$ is defined.

If the depth of a peak of the PDD in the deepest layer is defined as z0, the depth of the peak shifted in each layer is given as follows.

$$z\text{peak} = z0 - zi$$

According to the invention, when calibration is carried out at zpeak, a calibration factor $\alpha i$ is given as follows.

$$\alpha i = Di(z0-zi)/\{K0 \cdot d\text{MINIPEAK\_PHYS}(z0) \cdot Wi/\alpha i\}$$

$K0 \cdot d\text{MINIPEAK\_PHYS}(z0) \cdot Wi/\alpha i$ corresponds to the count value measured by the dose monitor.

As described above, while in the calibration method of the related art, the single calibration factor Gy/count is defined, in the calibration method of the invention, there are calibration factors by the number of layers. In the method of the related art, the calibration factor is determined only at one point on the center of the SOBP, thus the possibility that Gy/count differs between the layers is not considered.

In the method of the related art, the respective layers contribute to the single calibration value with different weights. The weight is proportional to a physical dose which is contributed to zC by the relevant layer.

$$K0 \cdot d\text{SOBP\_PHYS}(zC+zi) \cdot Wi$$

In a layer where dSOBP_PHYS(zC+zi) or Wi is small, the calibration factor is insensitive to DSOBP_PHYS(zC).

Here, the following discussion is considered.

The discussion is that "a layer where Wi is small contributes little to the dose, thus with regard to the relevant layer, it is not necessary to accurately determine the calibration factor".

However, this contradicts the original point of view that the calibration factor is determined on the basis of actual measurement.

If the calibration factor does not need to be determined separately for a shallow layer, it will be assumed that, even when the irradiation condition changes, sufficient reliability is obtained even when the value of Wi is calculated only by computation without depending on actual measurement. In particular, a layer shallower than zC contributes to calibration only through the tail by nuclear spallation.

That is, in the calibration method of the related art, like a proton beam, in the case of a PDD with no tail of nuclear fragmentation, all layers shallower than zC does not contribute to calibration. Further, a layer which has little contribution at zC may have increasing contribution at another depth.

For this reason, like the invention, calibration of each layer is preferably carried out at the position of the peak of each layer, such that improvement in accuracy of dose calibration and systematic understanding are obtained.

As described above, according to the invention, the layers are calibrated separately; however, actually (in particular, in the case of a carbon beam), the width of the Bragg peak is narrow, thus it may be difficult to carry out calibration at the Bragg peak of each layer.

Figure 8:
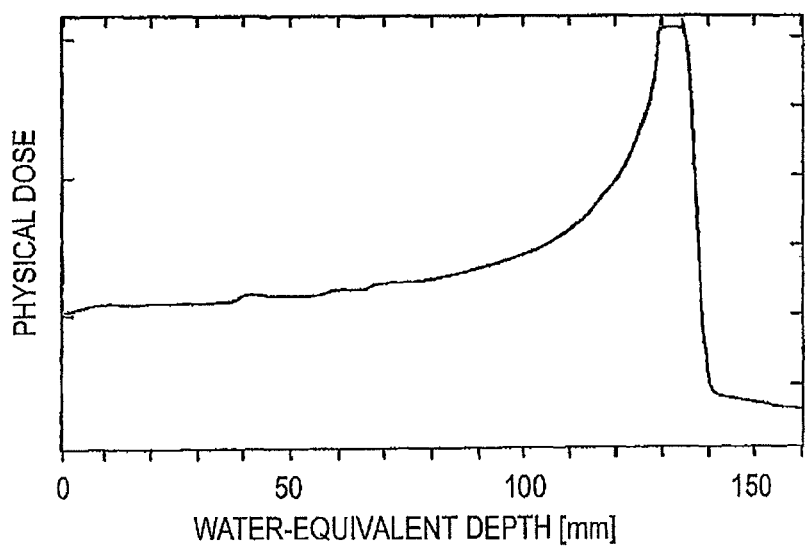
FIG. 8 is a diagram showing a mini-peak (physical dose) of a carbon beam.

Therefore, as another feature of the invention, it is assumed that, as shown in FIG. 8, a flat region where the physical dose distribution of a mini-ridge filter for use in laminated irradiation has the maximum value is formed.

FIG. 8 shows a mini-peak (physical dose) of a carbon beam.

Here, it is important to create a flat region of the PDD in the physical dose distribution.

The width of the PDD flat portion is defined as the width of the mini-peak. The width of the mini-peak needs to be greater than position accuracy which can be achieved at the time of dose calibration. The width of the mini-peak may be identical to the step width of the layer, but may not be necessarily identical.

Figure 9:
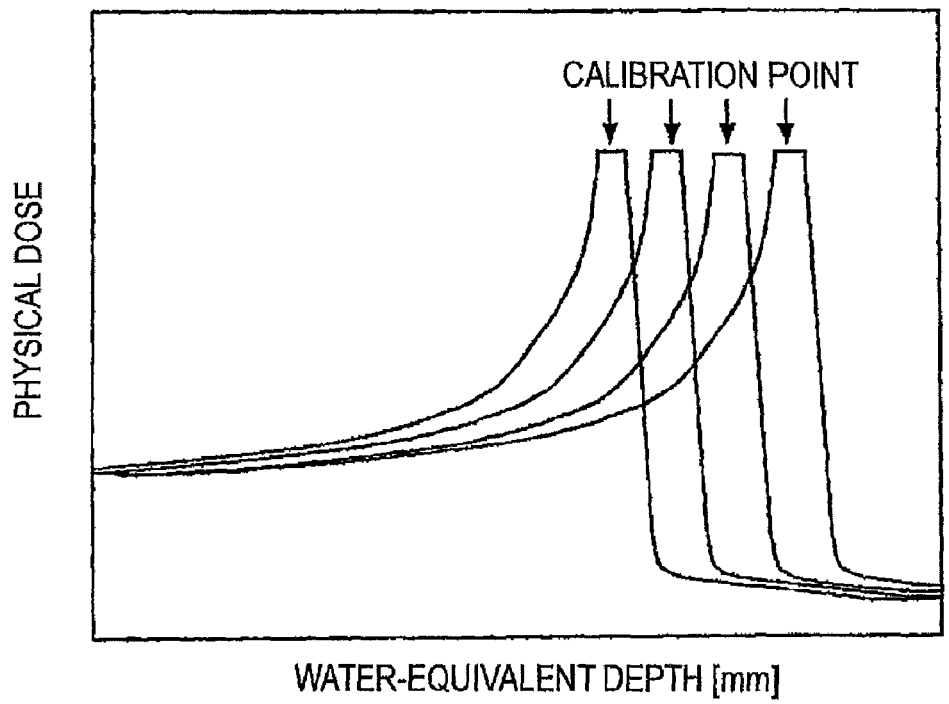
FIG. 9 is a diagram showing a position of a calibration point.

FIG. 9 schematically shows the calibration point of each layer.

In FIG. 9, for ease of understanding of the curve of the mini-peak, only selected curves are shown; however, actually, the flat portion of the mini-peak is nearby or superimposed.

Such a mini-ridge filter can be designed by using a known method.

For example, the shape of the physical dose PDD may be measured, the PDD curve may be shifted in accordance with the thickness of the ridge filter and added with a certain weight, and the weight may be optimized such that a desired flat region is formed.

In the calibration method of the related art, for each layer, calibration needs to be carried out after the depth position of the Bragg peak is accurately grasped. For this reason, at the time of calibration, calibration needs to be carried out after the Bragg curve in the depth direction is cautiously mapped.

Actually, the dose calibration measurement system may have insufficient mechanical accuracy with respect to required accuracy.

Alternatively, even when sufficient mechanical accuracy is obtained, it takes a lot of time and skill to obtain high accuracy every time.

Thus, in the related art, it is not practical to calibrate the layers separately by using the Bragg peak. For example, although the physical dose changes two or more times by a slight position error of 1 mm in the depth direction within the Bragg peak of the carbon beam, if the mini-peak having a width of 2 mm is created, the tolerance is significantly reduced.

As described above, according to this embodiment, even when dose calibration is carried out for each layer in laminated irradiation, the dose calibration can be carried out accurately in a short time.

The PDD of each layer for use in the dose calibration has the flat mini-peak in the physical dose, thus the dosimeter for use in calibration may be disposed at any position of the mini-peak. Therefore, a requirement for position accuracy at the time of measurement can be significantly reduced.

Next, treatment irradiation using the mini-ridge filter will be described.

Figure 10:
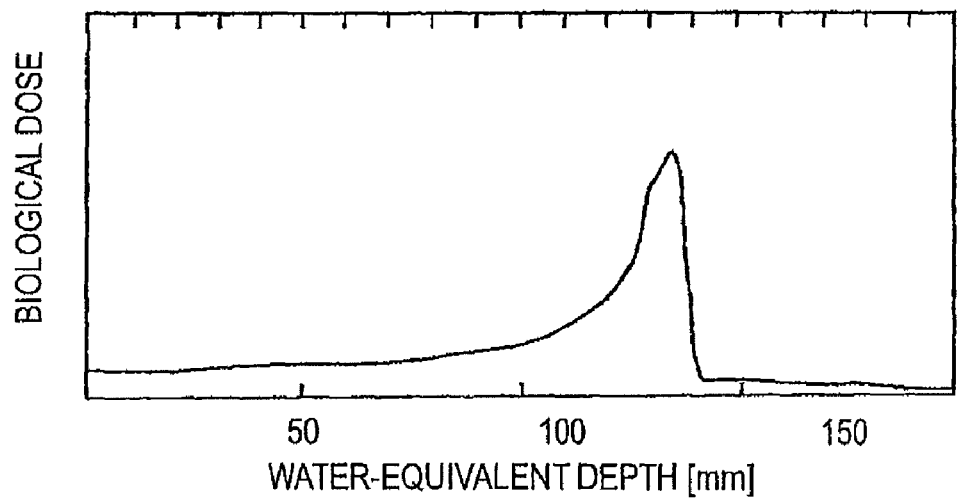
FIG. 10 is a diagram showing a mini-peak (biological dose) of a carbon beam.

If a flat peak is formed in the physical dose distribution, the peak of the biological dose distribution is as shown in FIG. 10, not flat.

However, the width of each layer is sufficiently narrow and the layers are superimposed, such that the SOBP can be formed in the biological dose.

For example, a mini-peak having a width of 5 mm may be superimposed at a step width of 2.5 mm.

While the dose steeply decreases on the deep side of the mini-peak, if a mini-ridge filter is designed to intentionally damp the steepness, the degree of flatness can be improved.

Meanwhile, in general, the biological dose preferably decreases as steeply as possible on the deep side when the SOB) is formed.

Figure 11:
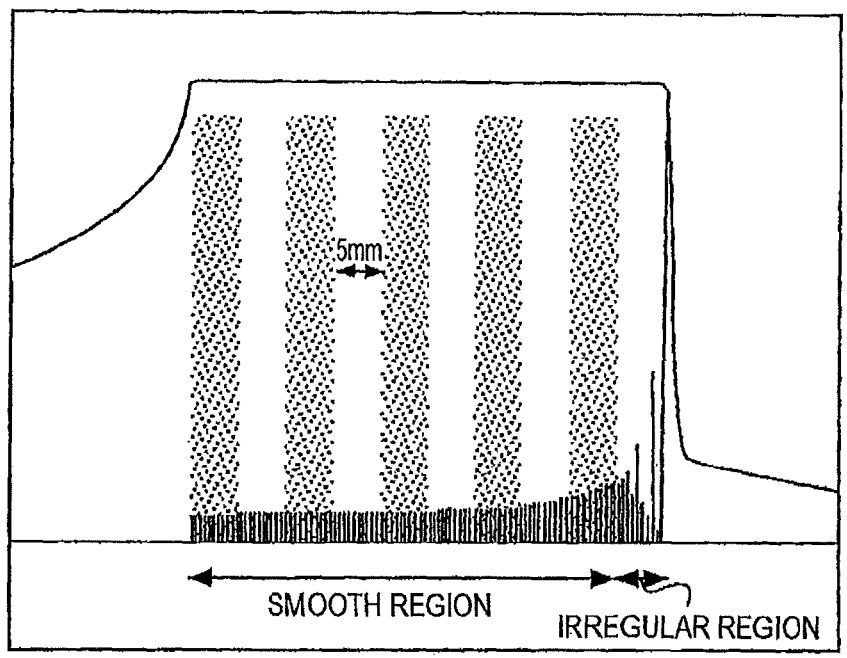
FIG. 11 is a diagram showing a weight of an extended Bragg peak of a carbon beam.

The weight of each layer for creating a uniform SOBP is examined. As shown in FIG. 11, it is known that the weight changes steeply near the deepest layer of the dose distribution (in the drawing, a region (plateau portion) where the weight is irregular), the weight does not almost change in a front region called plateau (in the drawing, a region where the weight is smooth) (see Non-Patent Citation 1).

For this reason, two kinds of ridge filters of a deepest layer-only mini-ridge filter for making the dose distribution of the deepest layer steep and a mini-ridge filter which is applied to a region where the weight is comparatively flat in front of the deepest layer-only mini-ridge filter are used. The degree of flatness of the SOBP can be improved and steepness of the PDD can be ensured.

Hitherto, although the description has been provided assuming that uniformity of the SOBP is ensured, other than the flat SOBP, a dose distribution in which the dose at the center portion of the SOBP increases may be desired.

In any tumor, a cancer cell having high resistance to radiation may exist at the center portion. In this case, irradiation may be desired to increase the dose of the center portion, instead of a uniform dose distribution.

The calibration method and the treatment irradiation method of the invention can respond to such a case.

Although in the above description, the laminated irradiation has been described, the same method can be applied to a method, called scanning irradiation, in which fine beams are irradiated.

In the scanning irradiation, in addition to lamination in the depth direction, fine beams (that is, particle beams) are also superimposed in the lateral direction.

In such a case, a mini-peak is formed in the depth direction by using the fine beams, such that dose calibration can be facilitated.

At this time, as a device for forming a mini-peak, a modulation wheel is appropriately used. This is because the fine beams are hard to uniformly hit a bar ridge filter.

When a bar ridge filter is used, it is necessary to narrow the pitch of the ridges.

Since the filter may have thin ridges, it is comparatively ease to make the pitch of the ridges narrow.

Alternatively, it may be considered that a bar ridge filter is vibrated, and beams are controlled to uniformly hit the bar ridge filter.

Similarly to laminated irradiation, the dose on the deep side of the mini-peak is intentionally damped, such that the degree of flatness can be improved. Further, two kinds of ridge filters of a deepest layer-only ridge filter and a plateau-only ridge filter are used together whereby the degree of flatness can be obtained without sacrificing steepness of the PDD.

As described above, according to the particle beam treatment apparatus of this embodiment, when a predetermined region of a target volume is divided into multiple layers in the depth direction of particle beams and particle beams are irradiated, dose calibration is carried out separately for the divided layers.

According to the particle beam treatment apparatus of this embodiment in which, when a predetermined region of a target volume is divided into multiple layers in the depth direction of particle beams and particle beams are irradiated, dose calibration is carried out separately for the divided layers, a physical dose distribution in the depth direction has a region, in which the dose becomes constant by using a mini-ridge filter, in at least a part of the width of each layer, and the dose calibration is carried out.

According to the particle beam treatment apparatus of this embodiment in which, when a predetermined region of a target volume is divided into multiple layers in the depth direction of particle beams and particle beams are irradiated, dose calibration is carried out separately for the divided layers, a physical dose distribution in the depth direction has a region, in which the dose becomes constant by using a mini-ridge filter, in at least a part of the width of each layer, and the target volume is irradiated while the layers are superimposed.

Embodiment 2

Next, Embodiment 2 will be described.

Although in Embodiment 1, an example where calibration is carried out for all of the layers has been described, the set conditions of the respective devices of the particle beam treatment apparatus do not change so much between the layers, but change slightly.

For this reason, as the actual irradiation results are accumulated, it is not necessary to carry out calibration for each layer, which has been described in Embodiment 1, for all of the layers every time.

In this case, the number of measurement points may be thinned.

As described above, the calibration points shown in FIG. 9 show the thinned state.

With regard to a thinned layer, the calibration value at one calibration point closest to the relevant layer may be extracted as it is, or the calibration value may be interpolated by using a plurality of calibration execution points nearby.

As a method of interpolation, various known methods, such as linear approximation or polynomial approximation may be used.

In mounting the calibration system, a function to allow a user to select whether to use all of the layers as calibration points or to carry out calibration with the layers thinned may be incorporated into a control system of the calibration system.

When the layers are thinned, it may be configured such that the user can select locations to be thinned, an interpolation algorithm, and the like.

According to this embodiment, the time necessary for calibration can be further reduced.

As described above, according to the particle beam treatment apparatus of this embodiment, dose measurement is carried out only for some layers selected from the multiple divided layers.

Embodiment 3

Next, Embodiment 3 will be described.

Figure 12:
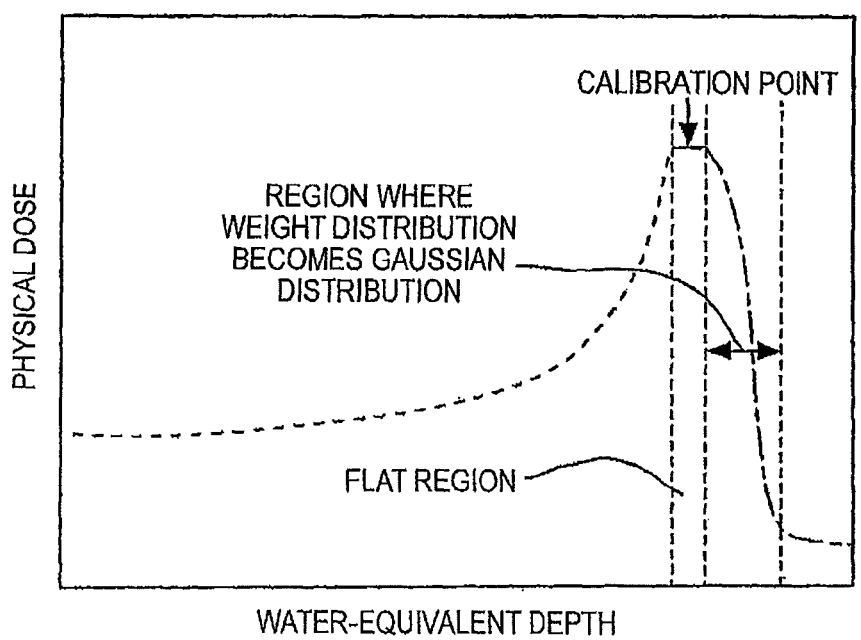
FIG. 12 is a diagram showing a design example of a mini-ridge filter according to Embodiment 3.
Figure 13:
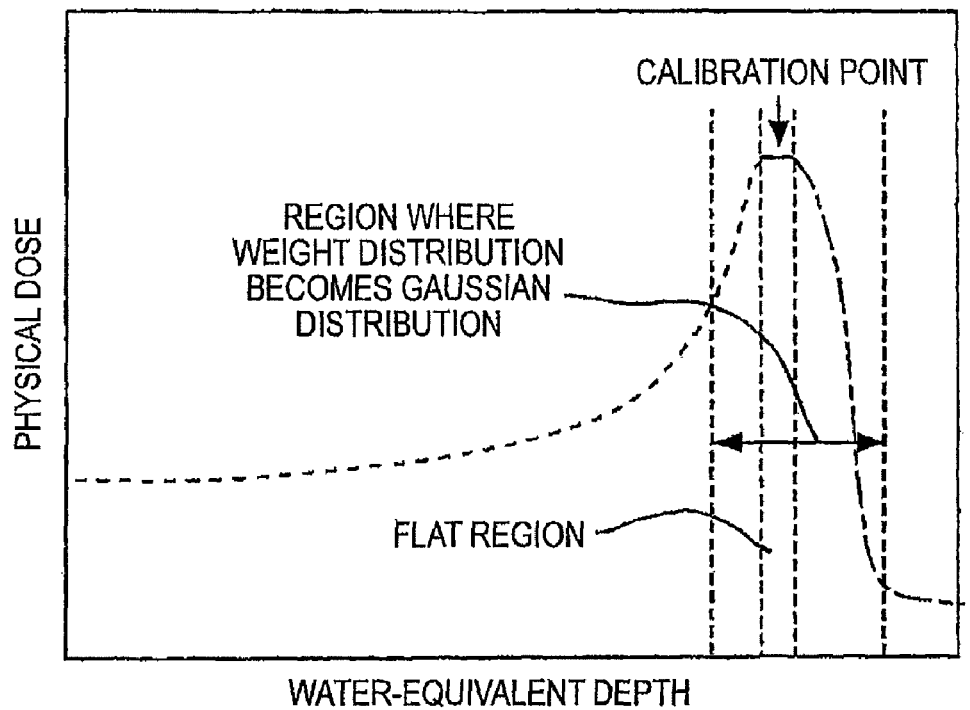
FIG. 13 is a diagram showing a design example of a mini-ridge filter according to Embodiment 3.
Figure 14:
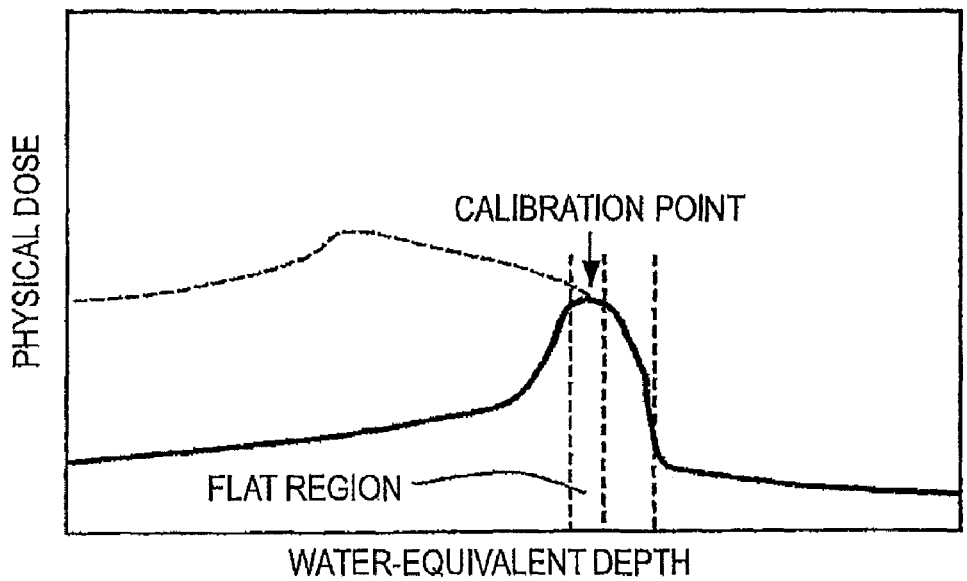
FIG. 14 is a diagram showing a design example of a mini-ridge filter according to Embodiment 3.

FIGS. 12 to 14 are diagrams illustrating a design example of a mini-ridge filter according to this embodiment.

In FIG. 12, a flat portion for dose calibration where the physical dose distribution is flat is provided in the front portion of the Bragg peak.

A deeper portion indicated by a dot-dash line is designed such that the weight of the Bragg peak has a Gaussian distribution. Thus, the relevant layer is smoothly superimposed on a deeper layer.

In FIG. 13, a flat portion for dose calibration where the physical dose distribution is flat is provided only at the center portion of the Bragg peak.

The flat portion is designed such that the weight of the Bragg peak has a Gaussian distribution. Thus, the relevant layer is smoothly superimposed on a deeper layer and a shallower layer.

In FIG. 14, the physical dose distribution (indicated by a dotted line) in which the biological dose shown in FIG. 4 corresponds to a flat dose distribution is reproduced at the deepest portion. Further, a mini-ridge filter is designed such that a flat region is provided in the physical dose distribution.

In the case of particle beam treatment, since the weight of the dose of the deepest portion is high, a mini-ridge filter is used which is specially optimized with respect to the dose distribution of the deepest portion, such that the dose distribution can be reproduced accurately even when the number of divided layers in the depth direction is small.

As described above, according to this embodiment, a flat mini-peak can be combined with another dose distribution shape by the physical dose. Therefore, superimposition of the layers can be facilitated, and the number of divided layers can be reduced.

INDUSTRIAL APPLICABILITY

The invention is suitable for implementing a particle beam treatment apparatus which can carryout dose calibration for respective layers in laminated irradiation, and can improve accuracy of dose calibration at the time of laminated irradiation.

The invention claimed is:

1. A particle beam treatment apparatus which divides a predetermined region of a target volume into multiple layers in a traveling direction of particle beams and irradiates the particle beams, the apparatus comprising:
    a particle beam irradiation section including a dose monitor which monitors a dose of the particle beams as a count value and forming an irradiation field in the predetermined region; and
    a treatment control section controlling the operation of the particle beam irradiation section in such a manner that when a calibration factor obtained for each layer by dividing a physical dose at the time of irradiating the particle beams for an i-th layer of the multiple layers by the count value is defined as $\alpha i$, and the count value reaches a value obtained by dividing a target dose for the i-th layer by the calibration factor $\alpha i$, the irradiation of the particle beams for the i-th layer is stopped, and irradiation is carried out for another layer other than the i-th layer.

2. The particle beam treatment apparatus according to claim 1, wherein the particle beam irradiation section includes a ridge filter which extends a Bragg peak in each of the multiple layers.

3. The particle beam treatment apparatus according to claim 2, wherein the treatment control section controls the operation of the particle beam irradiation section in such a manner that if the count value reaches a value expressed by the following equation (A), the irradiation of the particle beams for the i-th layer is stopped, and irradiation is carried out for another layer other than the i-th layer:

$$K0 \cdot d\text{MINIPEAK\_PHYS}(z0) \cdot Wi/\alpha i \qquad \text{Equation (A)}$$

wherein,
- $\alpha i$: a calibration factor obtained for each layer by dividing a physical dose at the time of irradiating the particle beams for an i-th layer of the multiple layers by the count value;
- K0: a standardization factor for obtaining a prescription dose;
- dMINIPEAK_PHYS ($z0$): a value of a peak of a physical dose PDD curve of a mini-peak in the deepest layer in the traveling direction of the particle beams;
- $z0$: a depth of a peak of the PDD curve of the mini-peak; and
- Wi: a dose weight for an i-th layer of the multiple layers.

4. The particle beam treatment apparatus according to claim 3, wherein the treatment control section sets a target dose to be irradiated for each of the multiple layers in accordance with the output of dose calculation which is carried out by a treatment planning section in advance.

5. The particle beam treatment apparatus according to claim 2, wherein the treatment control section sets a target dose to be irradiated for each of the multiple layers in accordance with the output of dose calculation which is carried out by a treatment planning section in advance.

6. The particle beam treatment apparatus according to claim 1, wherein the treatment control section sets a target dose to be irradiated for each of the multiple layers in accordance with the output of dose calculation which is carried out by a treatment planning section in advance.

* * * * *